United States Patent
Blumberg, Jr. et al.

(10) Patent No.: US 10,994,074 B2
(45) Date of Patent: May 4, 2021

(54) SYSTEM, METHOD, AND APPARATUS FOR DETECTING COUPLING TO A PATIENT USING ONE OR MORE ELECTRIC-FIELD SENSORS

(71) Applicant: DEKA Products Limited Partnership, Manchester, NH (US)

(72) Inventors: David Blumberg, Jr., Deerfield, NH (US); Michael F. Bellino, Bradford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 288 days.

(21) Appl. No.: 15/952,652

(22) Filed: Apr. 13, 2018

(65) Prior Publication Data
US 2018/0228964 A1 Aug. 16, 2018

Related U.S. Application Data

(62) Division of application No. 14/679,364, filed on Apr. 6, 2015, now Pat. No. 9,968,730.

(60) Provisional application No. 61/987,742, filed on May 2, 2014.

(51) Int. Cl.
*A61M 5/142* (2006.01)
*A61M 5/50* (2006.01)

(52) U.S. Cl.
CPC .......... *A61M 5/142* (2013.01); *A61M 5/5086* (2013.01); *A61M 2205/13* (2013.01); *A61M 2205/14* (2013.01); *A61M 2205/3317* (2013.01); *A61M 2205/6009* (2013.01); *A61M 2205/6054* (2013.01); *A61M 2230/04* (2013.01); *A61M 2230/06* (2013.01); *A61M 2230/60* (2013.01)

(58) Field of Classification Search
CPC ............ A61M 5/1723; A61M 5/14276; A61M 1/1086; A61M 5/172; A61B 5/14532; A61B 5/0205; A61B 5/0215; A61B 5/053; A61B 5/1495; A61B 5/4839; A61B 5/7275
See application file for complete search history.

(56) References Cited

U.S. PATENT DOCUMENTS

| 8,376,978 B2 * | 2/2013 | Roger | A61M 1/3661 |
| | | | 604/4.01 |
| 2008/0195060 A1 * | 8/2008 | Roger | A61M 1/3653 |
| | | | 604/246 |

OTHER PUBLICATIONS

Farnell, Electronics Weekly.com, "Body's electric near-field confirms user ID", http://www.electronicsweekly.com/news/design/communications/bodys-electric-near-field-confirms-user-id-2013-02, pp. 6, Apr. 2, 2015.

(Continued)

*Primary Examiner* — Manuel A Mendez
(74) *Attorney, Agent, or Firm* — James D. Wyninegar, Jr.

(57) ABSTRACT

A pump for infusing fluid, the pump including a pumping mechanism, a fluid delivery device, a plurality of electric field sensors, and a measurement component. The plurality of electric field sensors is configured to estimate either an electric field that is associated with a patient, or an electric field that is associated with a fluid path of the pump, or both. The measurement component is configured to receive the electric field estimates from each of the electric field sensors and further configured to measure the difference between the electric field estimates.

20 Claims, 8 Drawing Sheets

(56) References Cited

OTHER PUBLICATIONS

Zimmerman, T.G., "*Personal Area Networks: Near-field intrabody communication*", IBM Systems Journal, vol. 35, Nos. 3&4, 1996, 0018-8670/96/$5.00 ã 1996 IBM, pp. 609-617.

* cited by examiner

US 10,994,074 B2

SYSTEM, METHOD, AND APPARATUS FOR DETECTING COUPLING TO A PATIENT USING ONE OR MORE ELECTRIC-FIELD SENSORS

CROSS REFERENCE TO RELATED APPLICATIONS

This application is a divisional application of U.S. application Ser. No. 14/679,364, filed Apr. 6, 2015 and entitled System, Method, and Apparatus for Detecting Coupling to a Patient Using One or More Electric-Field Sensors, now U.S. Pat. No. 9,968,730, issued May 15, 2018, which claims the benefit of U.S. Provisional Patent Application Ser. No. 61/987,742, filed May 2, 2014 and entitled System, Method, and Apparatus for Detecting Coupling to a Patient Using One or More Electric-Field Sensors, which is hereby incorporated herein by reference in its entirety.

BACKGROUND

Relevant Field

The present disclosure relates to detecting whether an apparatus is coupled to a patient. More particularly, the present disclosure relates to a system, method, and apparatus for detecting whether an apparatus, for example an infusion pump or a dialysis machine, is coupled to a patient using one or more electric-field sensors.

Description of Related Art

Using a pump to infuse fluid into a patient generally requires tubing and a fluid delivery device (e.g., catheter, cannula, IV, etc.) be used to infuse the fluid into the patient. Despite the best efforts of professionals and caregivers (e.g., doctors, nurses, technicians, nurse practitioners, etc.), the tube through which the fluid is being infused may inadvertently become disconnected from the patient. The pump may continue to pump the fluids even though the patient is no longer connected, which, not only wastes fluid, but prevents the patient from receiving the much needed fluid. In the case of a hemodialysis pump, either the tube being used to pump blood from the patient, the tube being used to pump blood back into the patient, or both tubes may inadvertently become disconnected from the patient.

SUMMARY

A pump for infusing fluid, said pump comprising a pumping mechanism configured to pump fluid, a first electric field sensor configured to estimate a first electric field associated with a patient, a second electric field sensor configured to estimate a second electric field associated with said patient, wherein said first and second electric field sensors are configured to be operatively coupled to a fluid path of said pumping mechanism, and a measurement component configured to measure differences between said first electric field and said second electric field.

BRIEF DESCRIPTION OF THE DRAWINGS

These and other aspects will become more apparent from the following detailed description of the various embodiments of the present disclosure with reference to the drawings wherein.

DETAILED DESCRIPTION

In some embodiments, a pump as described herein refers to an infusion pump; however, other pumps may be used in various embodiments of the present disclosure, such as insulin pumps, dialysis pumps, etc. The pumps may utilize one or more electric-field sensors as described herein.

Figure 1:
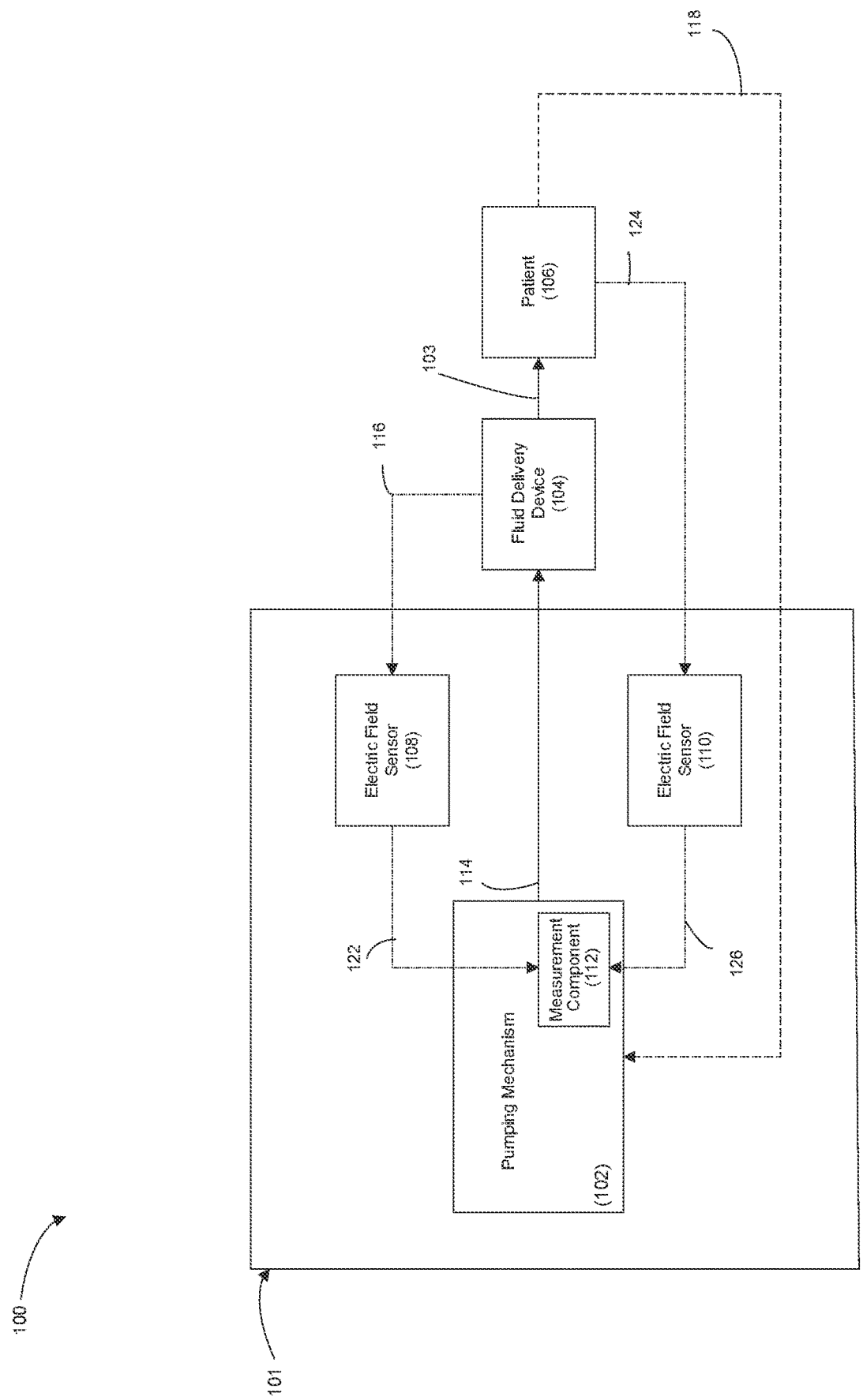
FIG. 1 is a block diagram of a system having a pump that utilizes two electric fields sensors to determine if the pump is coupled to a patient in accordance with an embodiment of the present disclosure.

FIG. 1 is a block diagram of a system 100 having a pump 101 that utilizes two electric-field sensors 108, 110 to determine if the pump 101 is coupled to a patient 106 in accordance with an embodiment of the present disclosure.

Referring to FIG. 1, a generalized view of a pump 101 is shown. The pump 101 is shown to include a pumping mechanism 102, two electric field sensors 108, 110 each configured to estimate an electric field, and a measurement component or circuit 112. A fluid delivery device 104 (e.g., catheter, cannula, IV, etc.) and a patient 106 are shown in the fluid path of the pump. The fluid path of the pump includes connections 114 and 103. The fluid path may also contain connection 118 if necessary to perform the treatment of the patient 106. Connections 116 and 124 show electric field sensors 108 and 110 estimating an electric field from both the fluid delivery device 104 and the patient 106, respectively.

In some embodiments, the electric field sensors 108 and 110 are configured to estimate either the magnitude of an electric field, or the flux of an electric field, or both. In some embodiments, the estimated electric field may be an electric field associated with a muscle of the patient 106, or, further, in some embodiments, the estimated electric field may be generated by electrical activity associated with the heart of the patient 106. In yet further embodiments, the estimated electric field may be associated with other biological electrical activity pertaining to other organs or tissue. Connections 122 and 126 show electric field sensors 108 and 110 respectively communicating the estimated electric field to the measurement component 112. The measurement component 112 may use the input received from the electric field sensors 108 and 110 through connections 122 and 126, respectively, to determine a heartbeat of the patient 106. The connections 116, 124, 122 and 126 may be wired connections, wireless connections, or a combination thereof, in some embodiments.

In some embodiments, the electric field sensor 108 may be on or near any part of the fluid path including, but not limited to, on or near the tubing, on or near the fluid delivery device 104, and on or near the pumping mechanism 102. In some embodiments, the measurement component 112 may be outside of the pumping mechanism 102. In some embodiments, if one of the electric field sensors 108 or 110 stopped communicating the estimated electric field, then the measurement component 112 may not be able to determine the heartbeat of the patient 106. One of the electric field sensors 108 or 110 may stop communicating its respective estimated electric field if the sensor was no longer able to estimate the electric field. The electric field sensor 108 may not be able to estimate the electric field if, for example, the fluid delivery device 104 became detached from the patient 106.

Figure 2:
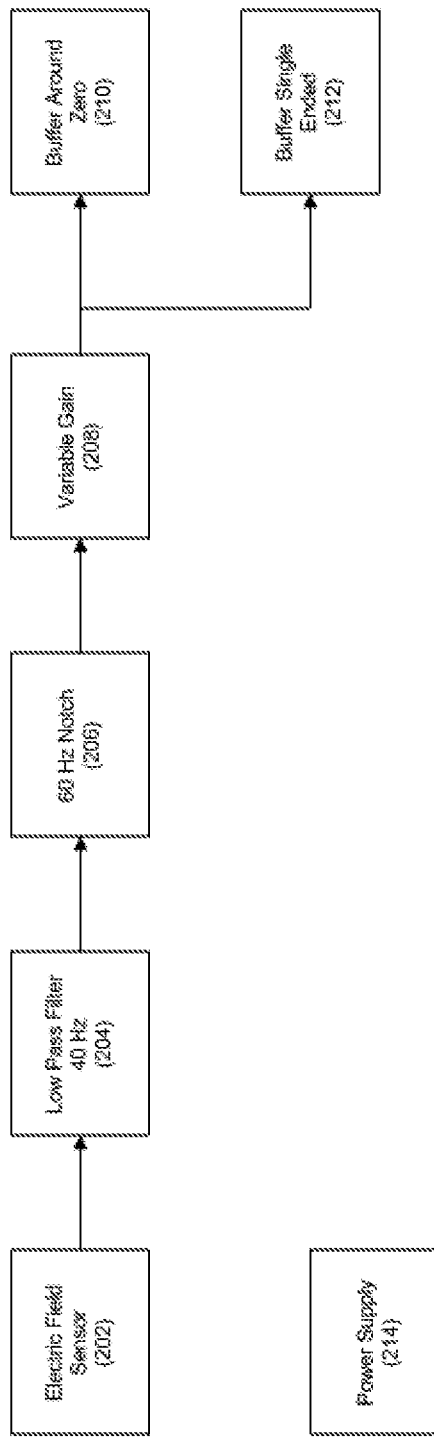
FIG. 2 is a block diagram of a system for processing an electric-field sensor in accordance with an embodiment of the present disclosure.

FIG. 2 is a graphical representation of a heartbeat detection circuit, part or all of the heartbeat detection circuit being included in the measurement component 112 of FIG. 1, in some embodiments. In some embodiments, the heartbeat detection circuit will receive input from the electric field sensor 202. The heartbeat detection circuit may also include a first signal filter 204, a second signal filter 206, a signal amplifier 208, a first buffer amplifier 210, and a second buffer amplifier 212. In some embodiments, the first signal filter 204 may allow signals with a frequency below a desired threshold to pass through the filter, while the filter attenuates the amplitude of any signals with a frequency greater than the desired threshold. The first signal filter 204 may be a low pass filter, and, in yet further embodiments, the low pass filter may have a cutoff threshold of 40 Hertz (Hz). The second signal filter 206 may allow signals with a frequency below or above a certain threshold pass through the filter, yet the filter may attenuate the amplitude of signals whose frequency matches the threshold frequency. In some embodiments, the second signal filter 206 is a band stop filter, while, in yet further embodiments, the second signal filter may be a 60 Hz notch filter, the filter attenuating signals having a frequency of 60 Hz. In some embodiments, the 60 Hz notch filter may be used to attenuate ambient noise. The signal amplifier 208 may be a variable gain amplifier. The variable gain amplifier 208 may utilize the power supply 214 in order to increase the amplitude of the signal coming from the second signal filter 206. The variable gain amplifier 208 may then output the signal to the two buffer amplifiers 210, 212. In some embodiments, the two buffer amplifiers are voltage buffer amplifiers. In yet other embodiments, the voltage buffer amplifiers may have a voltage gain of 1, or, in other words, be voltage followers. In some embodiments, although the buffer amplifiers 210, 212 may have a voltage gain of 1, they may have a larger gain as required.

Figure 3:
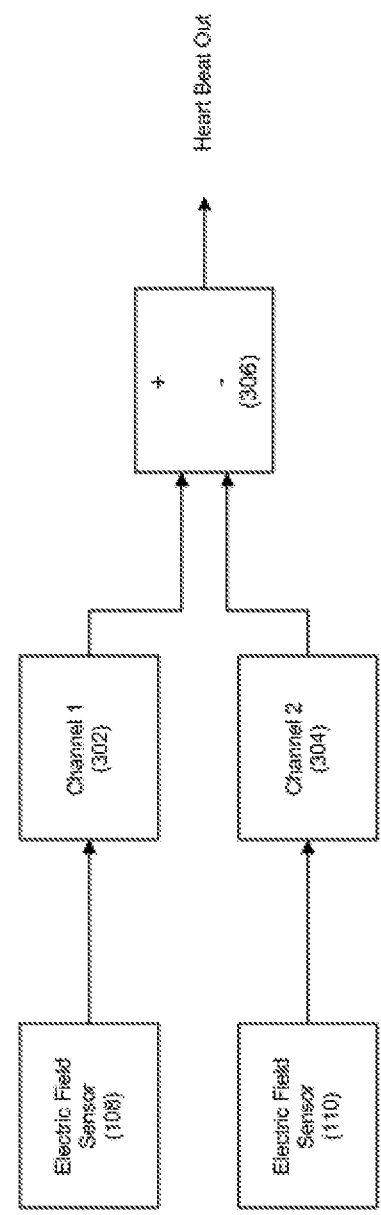
FIG. 3 is a block diagram of a system for detecting a heartbeat of patient using two electric-field sensors in accordance with an embodiment of the present disclosure.

FIG. 3 is a graphical representation of two heartbeat detection channels 302, 304 and a measurement component 306. Each heartbeat detection channel may each include a heartbeat detection circuit as depicted in FIG. 2. The first heartbeat detection channel 302 may receive an input signal from the electrical field sensor 108, and may send an output signal to the measurement component 306. Similarly, the second heartbeat detection channel 304 may receive an input signal from the electrical field sensor 110, and may send an output signal to the measurement component 306. The measurement component 306 may use the output signals of the first and second heartbeat detection channels 302, 304 to determine a heartbeat of a patient (e.g., the patient 106 of FIG. 1). In some embodiments the measurement component 306 may be a differential amplifier. The measurement component 306 may include an automatic gain control function.

Figure 4:
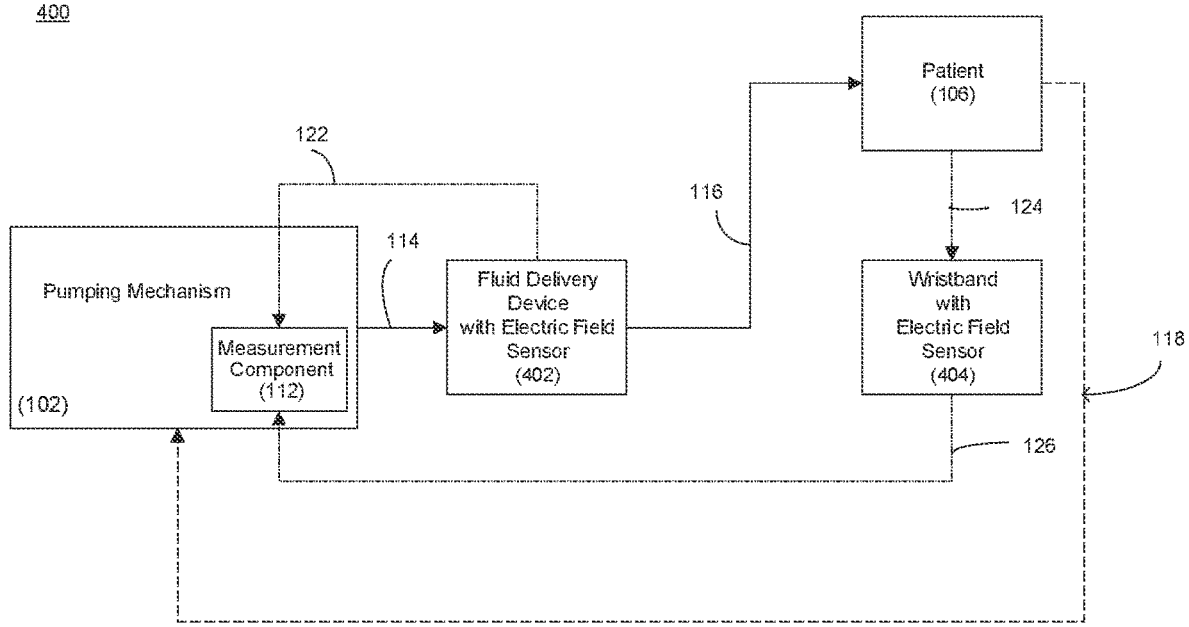
FIG. 4 is a block diagram of a system having a pump that has two electric-field sensors wherein one of the electric field sensors is coupled to a patient through a wristband and the other one of the electric-field sensors is part of a fluid delivery device to in accordance with an embodiment of the present disclosure.
Figure 5:
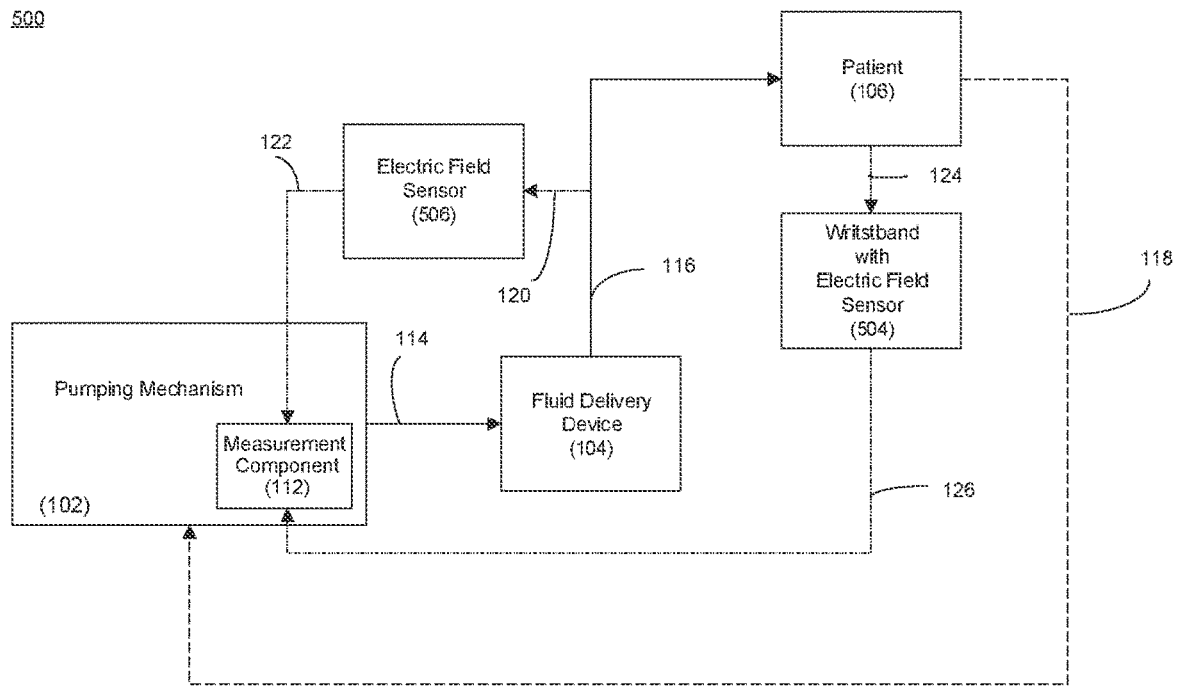
FIG. 5 is a block diagram of a system having a pump that has two electric-field sensors wherein one of the electric field sensors is coupled to a patient through a wristband and the other one of the electric-field sensors is coupled to a fluid path of a fluid delivery device in accordance with an embodiment of the present disclosure.
Figure 6:
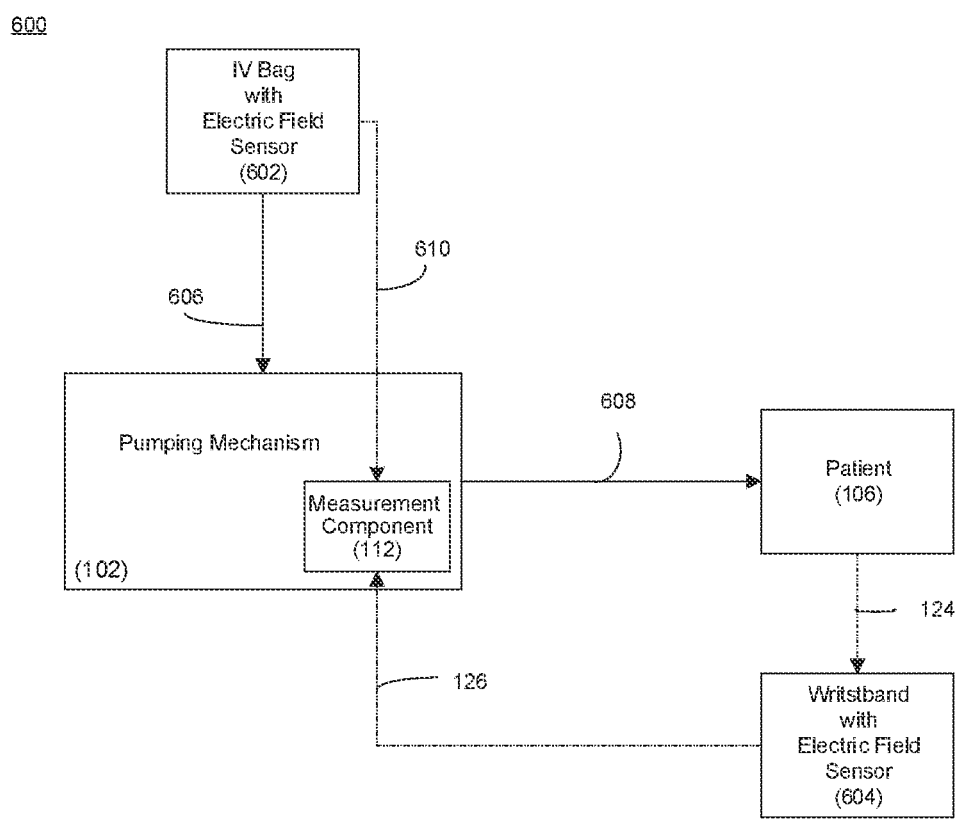
FIG. 6 is a block diagram of a system having a pump that is coupled to an IV bag with an electric-field sensor for infusing fluid into a patient and a wristband with another electric-field sensor coupled to the patient in accordance with an embodiment of the present disclosure.

Referring now to FIGS. 4-6, various embodiments are shown wherein the patient is wearing a wristband with an electric field sensor. Referring to FIG. 4, the patient may wear a wristband with an electric field sensor 404, and a second electric field sensor may be located on the fluid delivery device 402 in the fluid path of the pump 400. The fluid delivery device 402 may be a catheter, an IV bag, or other fluid delivery device, the second electric field sensor configured to estimate an electric field associated with the fluid delivery device 402. Similarly, the wristband with the electric field sensor 404 may be configured to estimate an electric field associated with the patient 106. Both the wristband with the electric field sensor 404 and the fluid delivery device with the second electric field sensor 402 may provide their respective electric field estimate to the measurement component 112, the measurement component 112 being part of the pumping mechanism 102 in some embodiments.

Referring to FIG. 5, the patient may wear a wristband with an electric field sensor 504, and a second electric field sensor 506 may be on or near the tubing in the fluid path of the pump 500. Similar to the wristband in FIG. 4, the wristband with the electric field sensor 504 in FIG. 5 may be configured to estimate an electric field associated with the patient 106. The wristband 504 may be further configured to communicate the estimate of the electric field to the measurement component 112. In some embodiments, the second electric field sensor 506 may be on or near the tubing near the fluid delivery device 104. The second electric field sensor 506 may be configured to estimate an electric field associated with the fluid path near the fluid delivery device 104. The second electric field sensor 506 may be further configured to communicate the estimate of the electric field to the measurement component 112.

Referring now to FIG. 6, in some embodiments, the pump 600 may include a wristband with an electric field sensor 604 that may be worn by the patient 106, and the pump 600 may further include an IV bag 602 with a second electric field sensor coupled thereto. The IV bag 602 may be in the fluid path of the pump 600 via fluid connection 606 between the IV bag 602 and the pumping mechanism 102, and via fluid connection 608 between the pumping mechanism 102 and the patient 106. Similar to the above mentioned embodiments, the electric field sensor on the IV Bag 602 may estimate an electric field associated with the fluid path of the pump 600 and communicate the estimate of the electric field to the measurement component 112. Similarly, the electric field sensor on the wristband 604 may estimate an electric field associated with the patient 106 and communicate the estimate of the electric field to the measurement component 112. The measurement component 112, as mentioned above, may use the input from each electric field sensor to determine a heartbeat associated with the patient 106.

Figure 7:
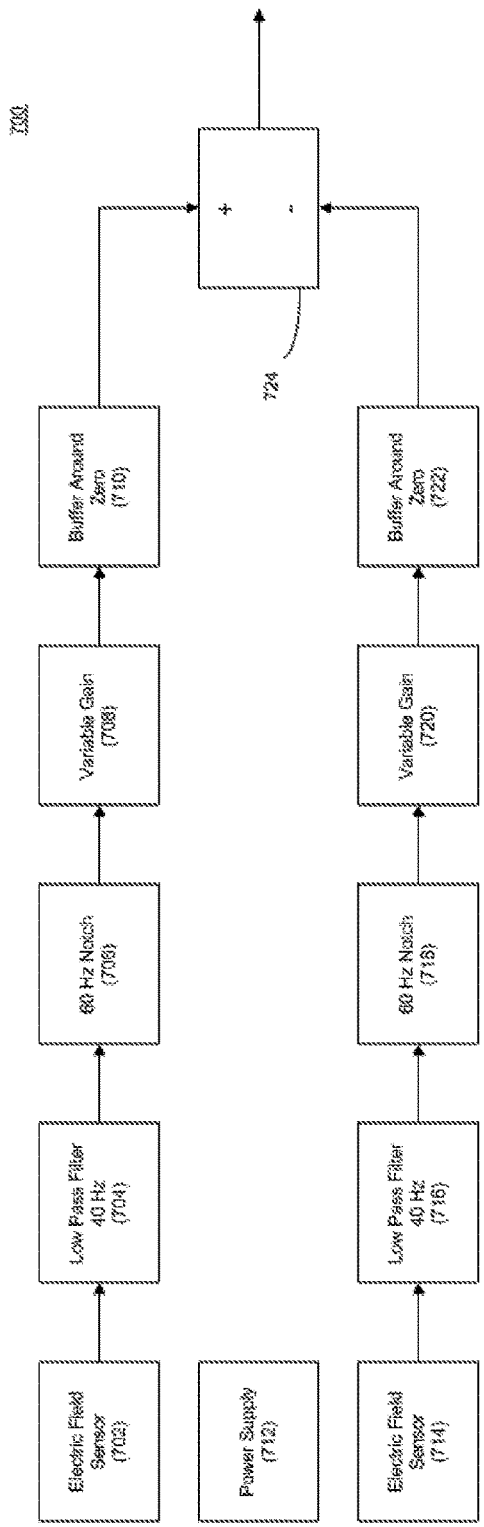
FIG. 7 is a block diagram of a circuit for muscle activity detection in accordance with an embodiment of the present disclosure.

FIG. 7 is a graphical representation of a muscle stimulation detection circuit 700. The muscle stimulation detection circuit 700 may include a first electric field sensor 702, a second electric field sensor 714, each of the first and second electric field sensors 702, 714 being operably connected to at least one signal filter and at least one signal amplifier. The first electric field sensor 702 and the second electric field sensor 714 may be configured to estimate an electric field associated with a first muscle portion and a second muscle portion, respectively. The first muscle portion, in some embodiments, may be near a first muscle extreme, while, similarly, the second muscle portion may be near a second muscle extreme. The first and second electric field sensors 702, 714 may each communicate their respective electric field estimates to a measurement component 724.

In some embodiments, the electric field estimates may be included in respective first and second output signals from the first and second electric field sensors 702, 714. The first output signal may be communicated from the first electric field sensor 702 to the measurement component 724 via the at least one signal filter and the at least one signal amplifier operably connected to the first electric field sensor 702. Similarly, the second output signal may be communicated from the second electric field sensor 714 to the measurement component 724 via the at least one signal filter and the at least one signal amplifier operably connected to the second electric field sensor 714. In some embodiments, the muscle stimulation detection circuit 700 may further include a power supply 712. The power supply 712 may be configured to allow each at least one signal amplifier to increase the amplitude of the output signal from the signal amplifier's respective electric field sensor. The measurement component 724 may be configured to determine a difference in electric field magnitude between the first muscle portion and the second muscle portion. In some embodiments, the measurement component 724 may be configured to determine a difference in electric field flux between the first muscle portion and the second muscle portion.

Figure 8:
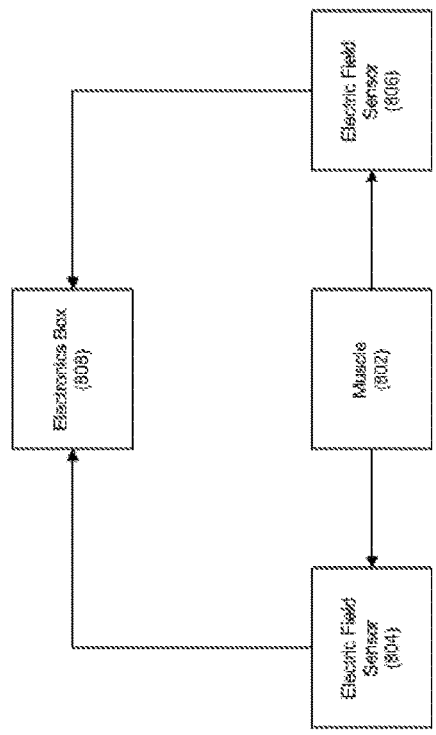
FIG. 8 is a block diagram of an apparatus for muscle activity detection in accordance with an embodiment of the present disclosure.

In some embodiments, the at least one signal filter and at least one signal amplifier for each electric field sensor, 702, 714, as well as the measurement component 724 may be contained in an electronics box 808 as depicted in FIG. 8. In some embodiments, the power supply 712 may also be included in the electronics box 808. FIG. 8 is a graphical representation of a muscle stimulation detection circuit, such as the stimulation detection circuit 700 of FIG. 7. The muscle stimulation detection circuit of FIG. 8 may include, in addition to the electronics box 808, a first electric field sensor 804 and a second electric field sensor 806. The first and second electric field sensors 804, 806 being operably engaged with a first portion and a second portion of a muscle 802, respectively. In some embodiments, the first and second electric field sensors 804 and 806 may be the first and second electric field sensors 702 and 714 of FIG. 7, respectively.

Figure 9:
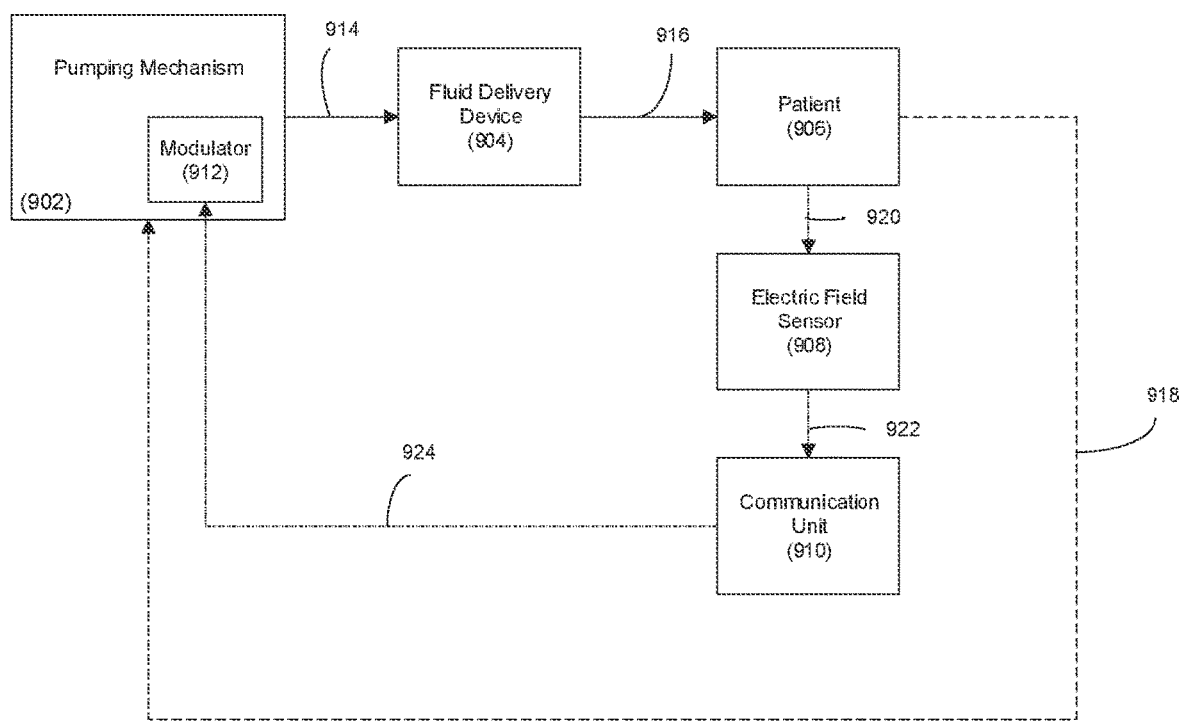
FIG. 9 is a block diagram of a system having a pump with an authentication circuit in accordance with an embodiment of the present disclosure.

Referring now to FIG. 9, a generalized view of a pump 900 with an authentication circuit is shown. In some embodiments, the authentication circuit may be used to identify a patient, a pump operator, or another person. The pump 900 is shown to include a pumping mechanism 902, which may include a modulator 912, an electric field sensor 908, and a communication unit 910 in communication with the modulator 912. In some embodiments, the modulator 912 may be located outside of the pumping mechanism 902. A fluid delivery device 904 (e.g., catheter, cannula, IV, etc.) and a patient 906 are shown in the fluid path of the pump. The fluid path of the pump includes connections 914 and 916. The fluid path may also contain connection 918 if necessary to perform the treatment of the patient. The modulator 912 may be operatively coupled to the patient 906, or the fluid path of the pump 900. As such, the modulator 912 may be configured to apply a modulated electric field to the patient 906, or to the fluid path of the pump 900. In some embodiments, the modulator 912 or the electric field sensor 908 may be operatively coupled to the patient 906 via another fluid path. Similarly, the electric field sensor 908 may be operatively coupled to the fluid path of the pump 900, or the patient 906, and, as such, the electric field sensor 908 may be configured to estimate an electric field associated with the patient 906, or with the fluid path of the pump 900, respectively. The connection 920 of FIG. 9 illustrates the electric field sensor 908 estimating an electric field from the patient 906. Connections 922 and 924 show communication unit 910 receiving the estimated electric field from electric field sensor 908 and communicating the estimated electric field to the modulator 912.

The connections 920, 922 and 924 may be wired connections, wireless connections, or in some embodiments, a combination thereof. The modulator 912 may be configured to provide a modulated electric field to the fluid path of the pumping mechanism 902. In some embodiments, the modulator 912 may be configured to apply a modulated electric field to the patient 906. In some embodiments, the modulator 912 may be configured to inject a signal into the patient 906, the communication unit 910 being configured to recover the signal and subsequently communicate the signal back to the modulator 912. In some embodiments, the signal may comprise a number. The communication unit 910 may also be configured to communicate at least one command to the modulator 912. In some embodiments, the communication unit 910 may be configured to communicate an alert to the modulator 912 if the communication unit 910 does not recover the signal from the modulator 912. The modulator 912 may be further configured to output an error condition if the modulator 912 does not receive the recovered signal from the communication unit 910, or if the communication unit 910 communicates an alert to the modulator 912.

In some embodiments, the communication unit 910 may also communicate a command for the pump 900. In some embodiments, electric field sensor 908 may be on or near any part of the fluid path including, but not limited to, on or near the tubing, on or near the fluid delivery device, on or near the pumping mechanism, and on or near the patient. In some embodiments, the communication unit 910 may be located within the pumping mechanism 902.

Figure 10:
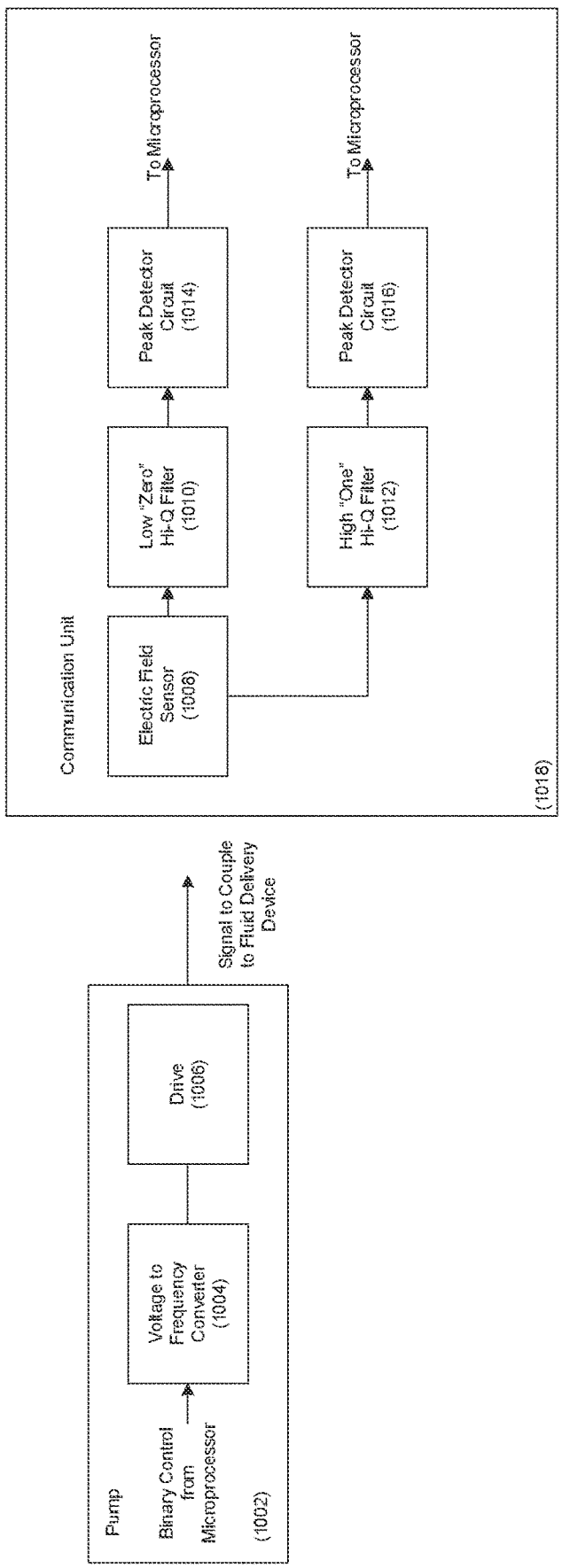
FIG. 10 is a block diagram of an authentication circuit in accordance with an embodiment of the present disclosure.

FIG. 10 is a graphical representation of how an authentication circuitry may work to provide a secure system for giving commands to a medical pump. The authentication circuitry may comprise a pump 1002 and a communication unit 1018 operably connected to the pump 1002. The communication unit 1018 may be operably connected to the pump 1002 by way of an electrical signal pathway as depicted in FIG. 10. The electrical signal pathway may include transmission of an electrical signal through a medium. In some embodiments, the medium may include the body of a person, or, further, the medium may include the body of a patient. In some embodiments, the pump 1002 may be the pumping mechanism 902 as depicted in FIG. 9, and the communication unit 1018 may be the communication unit 910 as also depicted in FIG. 9. The pump 1002 may include a source of binary control such as a microprocessor, a voltage-to-frequency converter 1004 and a drive component 1006. The voltage-to-frequency converter 1004 may be used to convert the digital binary control from a microprocessor within the pump 1002 to an analog signal. The drive component 1006 may take the analog signal from the voltage-to-frequency converter 1004 and broadcast the signal through the electrical signal pathway such that the analog signal can be received by the communication unit 1018. The analog signal from the drive component 1006 may be detected by an electrical field sensor 1008, which, in some embodiments, may be part of the communication unit 1018, or, in other embodiments, may be separate from the communication unit 1018. Further, in some embodiments, the electric field sensor 1008 may be the electric field sensor 908 as depicted in FIG. 9.

The communication unit 1018 may comprise a first signal filter 1010 that is configured to receive the detected analog signal from the electric field sensor 1008, and a first peak detector circuit 1014 that is operably connected to the signal filter 1010. The communication unit 1018 may further include a second signal filter 1012 that is configured to receive the detected analog signal from the electric field sensor 1008, and a second peak detector circuit 1016 that is operably connected to the signal filter 1012. The first and second signal filters, in some embodiments, may be band pass filters, each filter configured to allow a different range of frequencies to pass through.

In some embodiments, the first signal filter may be configured to allow a range of frequencies to pass through that is lower than the range of frequencies that the second signal filter is configured to allow to pass through. Each of the first and second band pass filters may be configured to operably engage with the first and second peak detector circuits, respectively, to convert the detected analog signal into a digital binary signal. Each of the first and second peak circuit detectors may output a digital signal to a microprocessor. The microprocessor may pass the digital signal from each of the first and second peak detector circuits through a threshold detector. In some embodiments the threshold detector may determine each time the digital signal from the first peak detector circuit crosses a lower threshold, and each time the digital signal from the second peak detector circuit crosses an upper threshold. Each time the digital signal from the first peak detector circuit crosses the lower threshold, the microprocessor may identify that occurrence as representing a "0" in the digital binary signal. Similarly, each time the digital signal from the second peak detector circuit crosses the upper threshold, the microprocessor may identify that occurrence as representing a "1" in the digital binary signal.

Figure 11:
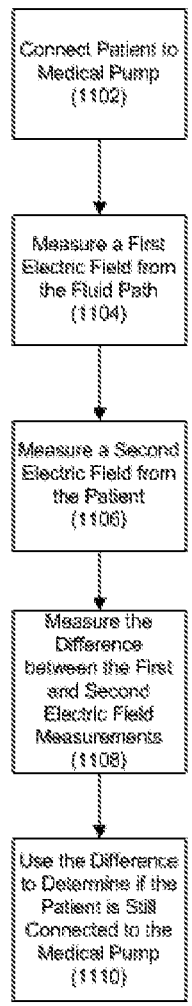
FIG. 11 is a flowchart diagram illustrating a method for detecting whether a patient is in the fluid path of the pump in accordance with an embodiment of the present disclosure.

Referring now to FIG. 11, a method for detecting whether a patient is in the fluid path of a medical pump is shown. At step 1102, a patient is connected to the pump. Next, at step 1104, a first electric field associated with a patient is measured from the fluid path of the pump; then, at step 1106, a second electric field associated with the patient is measured from the patient. In some embodiments, the first electric field of step 1104 may be measured from the patient, and the second electric field of step 1106 may be measured from the fluid path. In some embodiments, the first electric field of step 1104 and the second electric field of step 1106 may be determined or measured by a first electric field sensor and a second electric field sensor, respectively. In step 1108, the differences between the first and second electric field measurements are determined, and, in step 1110, those differences are used to determine if the patient is still in the fluid path of the pump (i.e., the patient is still connected to the medical pump). In some embodiments, if the patient is still detected, the method may repeat steps 1104-1110. In some embodiments, if the patient is not detected, the method may proceed to warning a healthcare professional that the patient is not detected or shutting down the pump. In some embodiments, a healthcare professional may be warned in a variety of ways including, but not limited to, emitting an alarm, sending a message to a healthcare professional electronically (e.g., by phone, email, pager, etc.), and dialing an emergency number.

Figure 12:
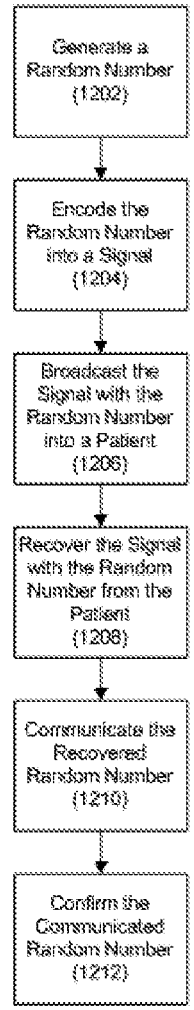
FIG. 12 is a flowchart diagram illustrating a method for authenticating a command for the pump in accordance with an embodiment of the present disclosure.

In some embodiments, the method may further include authenticating a command for the medical pump, as referred to in FIG. 12. The method for authenticating a command may include generating a random number in step 1202, encoding the random number into a signal in step 1204, and broadcasting the signal containing the random number into a patient in step 1206. In some embodiments, the broadcasting may occur through a fluid delivery device. The method of FIG. 12 may further include delivering the signal to a communication unit which may recover the signal and the random number from the patient in step 1208, the communication unit communicating the recovered random number from the recovered signal to the medical pump in step 1210, and confirming that the communication unit communicated the random number in step 1212. In some embodiments, the communication unit may communicate at least one command to the medical pump along with the recovered random number in step 1210. In further embodiments, the medical pump may output an error condition if the medical pump does not receive the random number from the communication unit. In some embodiments, the error condition may be output if the medical pump cannot confirm that the communication unit communicated the random number to the medical pump in step 1212.

Various alternative and modifications can be devised by those skilled in the art without departing from the disclosure. Accordingly, the present disclosure is intended to embrace all such alternatives, modifications, and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods, and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted o the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A pump for infusing fluid, the pump comprising:
a pumping mechanism configured to pump fluid;
a modulator configured to provide a modulated electric field, wherein the modulator is configured to apply the modulated electric field to at least one of a fluid path of the pumping mechanism and a patient;
an electric-field sensor configured to estimate an electric-field magnitude associated with the patient, wherein the electric-field sensor is configured to be operatively coupled to at least one of a fluid path of the pumping mechanism and the patient; and
a measurement component operatively coupled to the electric-field sensor to receive the estimate of the electric-field magnitude.

2. The pump according to claim 1, further comprising a communication unit in communication with the modulator.

3. The pump according to claim 2, wherein the communication between the communication unit and the modulator is a type of communication from the group consisting of wireless communication and wired communication.

4. The pump according to claim 1, wherein the modulator is configured to inject a signal with a random number into the patient.

5. The pump according to claim 4, further comprising a communication unit in communication with the modulator, wherein the communication unit is configured to recover the random number and communicate the random number.

6. The pump according to claim 5, wherein the communication unit is configured to communicate at least one command to the modulator.

7. The pump according to claim 5, wherein the communication unit is configured to communicate an alert to the modulator if the communication unit does not receive the random number.

8. The pump according to claim 7, wherein the modulator is configured to output an error condition if the modulator does not receive the random number from the communication unit.

9. The pump according to claim 1, wherein the modulator is operatively coupled to the patient and the electric-field sensor is operatively coupled to the fluid path.

10. The pump according to claim 9, wherein the modulator is operatively coupled to the patient via another fluid path.

11. The pump according to claim 1, wherein the modulator is operatively coupled to the fluid path and the electric-field sensor is operatively coupled to the patient.

12. The pump according to claim 11, wherein the electric-field sensor is operatively coupled to the patient via another fluid path.

13. A method for infusing fluid, the method comprising:
connecting a patient to a medical pump;
determining a first electric-field magnitude measurement associated with the patient;
determining a second electric-field magnitude measurement associated with the patient;
measuring a difference between the first and second electric-field magnitude measurements; and
using the difference to determine whether the patient is connected to the medical pump.

14. The method of claim 13, wherein the determining the first electric-field magnitude measurement is performed by a first electric field sensor and the determining the second electric-field magnitude measurement is performed by a second electric field sensor.

15. The method of claim 14, further comprising authenticating a command for the medical pump.

16. The method of claim 15, wherein the authenticating a command comprises:
generating a random number;
encoding the random number into a signal;
broadcasting the signal into the patient through a fluid delivery device;
delivering the random number to a communication unit;
communicating at least one command and the random number to the medical pump from the communication unit; and
confirming the communication unit communicated the random number.

17. The method of claim 16, wherein authenticating the command further comprises outputting an error condition if the medical pump does not receive the random number.

18. The method of claim 14, further comprising providing a warning upon a determination that the patient is not connected to the medical pump.

19. A system for infusing fluid, the system comprising:
a pumping mechanism configured to pump fluid;
a first electric field sensor configured to estimate a first electric-field magnitude associated with a patient;
a second electric field sensor configured to estimate a second electric-field magnitude associated with the patient, wherein the first and second electric field sensors are configured to be operatively coupled to a fluid path of the pumping mechanism; and
a measurement component configured to measure differences between the first electric-field magnitude and the second electric-field magnitude.

20. A pump infusing fluid, the pump comprising:
a pumping mechanism configured to pump fluid;
a first electric field sensor configured to estimate a first electric-field magnitude associated with a patient;
a second electric field sensor configured to estimate a second electric-field magnitude associated with the patient, wherein the first and second electric field sensors are configured to be operatively coupled to a fluid path of the pumping mechanism; and
a measurement circuit configured to measure differences between the first electric-field magnitude associated with the patient and the second electric-field magnitude associated with the patient.

* * * * *